United States Patent [19]

Watson

[11] Patent Number: 4,871,249

[45] Date of Patent: Oct. 3, 1989

[54] LIGHT COLLECTING DEVICE WITH CHAMBER INCLUDING ELLIPSOIDAL SURFACE AND SPHERICAL SURFACE

[75] Inventor: James V. Watson, Great Shelford, United Kingdom

[73] Assignee: Medical Research Council, Cambridge, England

[21] Appl. No.: 214,192

[22] Filed: Jul. 1, 1988

[30] Foreign Application Priority Data

Jul. 10, 1987 [GB] United Kingdom ............... 8716285

[51] Int. Cl.$^4$ ................... G01N 21/53; G01N 21/64; G01N 21/85; G02B 17/06
[52] U.S. Cl. .................................. 356/73; 350/619; 350/630
[58] Field of Search .................. 350/619, 630; 356/73, 356/72, 338, 318

[56] References Cited

U.S. PATENT DOCUMENTS 4,084,887  4/1978  Sigler .................................. 350/619
4,189,236  2/1980  Hogg et al. ........................ 356/338
4,710,638 12/1987  Wood ................................. 350/619

Primary Examiner—Jon W. Henry
Attorney, Agent, or Firm—Lee, Mann, Smith, McWilliams & Sweeney

[57] ABSTRACT

A light collecting device for flow cytometry comprises an internally reflecting chamber for collecting light from a point source within the chamber over a solid angle of substantially 4 pi and directing all the collected light through an exit point at or adjacent the wall of the chamber. The chamber comprises an ellipsoidal surface extending over a solid angle of substantially 2 pi and a spherical surface extending over a solid angle of substantially 2 pi, the firsts conjugate focus of the ellipsoidal surface being coincident with the center of curvature of the spherical surface and the second conjugate focus of the ellipsoidal surface being at the center point of the spherical surface. A capillary bore passes through the first conjugate focus to accommodate a sample stream which is illuminated by laser light to produce fluorescence at the first conjugate focus.

8 Claims, 2 Drawing Sheets

LIGHT COLLECTING DEVICE WITH CHAMBER INCLUDING ELLIPSOIDAL SURFACE AND SPHERICAL SURFACE

FIELD OF THE INVENTION

This invention relates to a light collecting device for use in any application which requires high efficiency light emission or collection from a source which is "small" (and therefore referred to herein as a point source) compared with the dimensions of the device. Specific applications include smoke, fire, chemical vapour and intrusion alarm systems; fibre-optic input and optical communications; projection and light condensing systems in cinematographics, microfilms, slide projection, microscopy, integrated circuit mask projection, warning beacons (e.g. marine lighthouses); flash photolysis systems; laser pumping; in both arc-lamp and laser based confocal microscopy systems and, most importantly, in flow cytometry with both arc-lamp and laser based systems.

THE INVENTION

According to the invention, there is provided a light collecting device comprising an internally reflecting chamber for collecting light from a point source within the chamber over a solid angle of substantially 4 pi and directing all the collected light through an exit point at or adjacent the wall of the chamber, said chamber being in the form of an ellipsoidal surface extending over a solid angle of substantially 2 pi and a spherical surface extending over a solid angle of substantially 2 pi, the first conjugate focus of the ellipsoidal surface being coincident with the centre of curvature of the spherical surface and the second conjugate focus of the ellipsoidal surface being located at or adjacent the spherical surface at the centre point of the curved surface area thereof, whereby in use light from a point source located at the said first conjugate focus is directed through the said second conjugate focus, some by virtue of a single reflection at the ellipsoidal surface and the rest by virtue of an initial reflection at the spherical surface followed by a reflection at the ellipsoidal surface.

THEORY OF THE INVENTION

The invention will be understood by making reference to FIGS. 1 and 2 of the accompanying drawings. First, consider the ellipsoidal reflector depicted in FIG. 1. Any light emitted from the first conjugate focus A will, after reflection, pass through the second conjugate focus B. Now, let the distance AB be equal to AC, and replace the ellipsoidal reflecting surface to the right of AC with a spherical reflecting surface of radius AB equal to AC centered at A. This is shown in FIG. 2. All light emitted from point A to the left of the line AC will be reflected through point B as before. All light emitted from point A to the right of the line AC will be reflected back on itself and subsequently will be reflected through point B after striking the ellipsoidal surface. Nominally, by including a small aperture at B, greater than 96 per cent of light emitted from point A can be collected.

FURTHER FEATURES OF THE INVENTION

In a practical embodiment, the ellipsoidal and spherical surfaces connect through a waist, more particularly an axially-short cylindrical surface for most applications, which is used for mounting the device. This means that, in the practical embodiment, the radius of curvature of the spherical surface is very slightly less than the distance between the conjugate foci of the ellipsoidal surface, owing to encroachment of the waist into the said ellipsoidal surface.

In some applications, such as flow cytometry, a polished light exit pupil is provided in the region of the exit point, cut into the spherical surface with a centre of curvature at the exact exit point, so that all light rays reflected from the ellipsoidal surface are normal to the surface of the pupil. In this way, it is ensured that the entire optical system is non-refracting and hence completely achromatic.

For flow cytometry, a capillary bore of small cross-sectional area, for example a square 250 by 250 micrometres bore, passes through the said first conjugate focus to accommodate the sample stream. Illumination to produce fluorescence at the said first conjugate focus may be by way of laser light directed through the waist or arc-lamp light directed through the exit point to be focussed at the first conjugate focus. It will thus be appreciated that, in the latter case, the illuminating path is the same as the light collecting path, but in the opposite direction. The device is thus well suited to epi-fluorescence microscope applications.

For light projection applications, the exit pupil may simply be a circular gap in the spherical surface. The waist region can serve for introduction of light, for example from a high pressure mercury arc lamp.

As will be appreciated from the foregoing, the light collecting device is especially suited to use in flow cytometry, and the invention is also concerned with a method of and apparatus for flow cytometry wherein the light collecting device is used for collection of the fluorescent light.

In a preferred embodiment of the light collecting chamber for flow cytometry, the chamber is formed from laser grade fused silica or quartz, and incorporates integral end discs which are interconnected by the capillary bore which passes through the first conjugate focus (itself coincident with the centre of curvature of the spherical surface). In the complete apparatus, the input and output sample tubes seal against the end discs by means of 0-rings or the like. The waist is formed by an annular plate, for example 2.5 mm thick in the axial direction, and serves for mounting, for example in a microscope, and also for input of the light beam in the case of laser illumination. The chamber is silvered except at the waist and exit pupil, and the silvered surface is preferably black lacquer coated for protection. In use, the sample flows through the capillary bore and is illuminated at the point of the first conjugate focus. The fluorescent light emitted is collected and detected at the exit point. Hitherto, flow cytometry in an epi-flourescence microscope has been difficult to put into practice because of the comparative inefficiency of the optics; the light collection chamber of this invention for the first time readily enables flow cytometry to be practised in an epi-fluorescence microscope.

DESCRIPTION OF DRAWINGS

A light collecting chamber in accordance with the invention is exemplified in the following description, making reference to the accompanying drawings, in which.

DESCRIPTION OF EMBODIMENT

Figure 1:
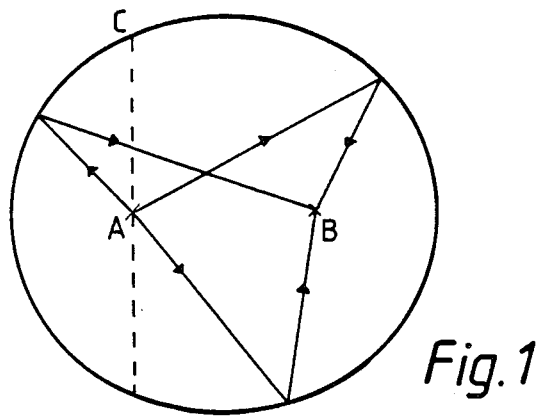
FIGS. 1 and 2 are diagrams to assist understanding the theory of the invention.
Figure 2:
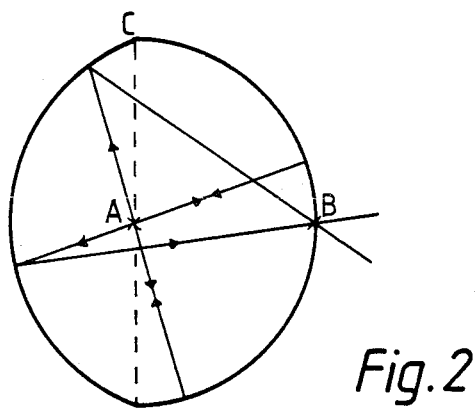
Figure 3:
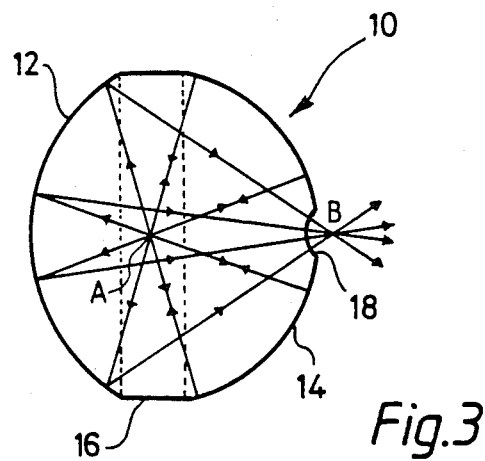
FIG. 3 is a diagrammatic view of a practical light collecting device in accordance with the invention.

The light collecting chamber of FIG. 3 will be understood by cross reference to the foregoing description of FIGS. 1 and 2.

Referring to FIG. 3, the light collecting chamber 10 comprises an ellipsoidal internally reflecting part 12 and a spherical internally reflecting part 14. The first and second conjugate foci of the ellipsoidal part are referenced A and B, respectively, in like manner to FIGS. 1 and 2. However, the radius of curvature of the spherical reflector 14 is slightly less than the distance AB between the conjugate foci of the ellipsoidal reflector, in order to allow for encroachment of a mounting waist 16 into the ellipsoidal part of the device. The exit pupil of the device is referenced 18. Apart from a small loss due to the presence of the waist 16 and the exit pupil 18, both the ellipsoidal reflector and the spherical reflector reflect light over a solid angle of substantially 2 pi.

FIG. 3 also shows the paths taken by typical light rays emanating from a source at the point A. Light emitted towards the left of the point A is reflected from the ellipsoidal reflector 12 directly to the second conjugate focus B. Light emitted towards the right of the point A is returned through the point A by the spherical reflector 14, thereafter to be reflected by the ellipsoidal reflector 12 to the point B.

The light exit pupil 18 is a polished pupil cut into the surface of the spherical reflector 14 so that all light rays pass normally through it, hence rendering the system non-refracting and thus achromatic.

In a practical construction, the following features and dimensions are applicable:

(1) The material employed is laser grade fused silica (Suprasil) or quartz and the whole chamber is of integrated construction.

(2) Although the absolute size of the device is not important, the ratio of the major-to-minor axes of the ellipsoidal surface is between 1.05 and 1.2 to 1, preferably 1.0987. Referring back to FIG. 1, this is the ratio at which the distance AB=AC.

(3) In one particular device, the long and short axis diameters of the ellipsoidal surface are 16.899 mm and 15.382 mm, respectively.

(4) The distance between the conjugate foci of the ellipsoidal reflector is 7.0 mm.

(5) The radius of curvature of the spherical reflecting surface centered at point A is 6.452 mm.

(6) The diameter across the waist is 12.659 mm.

(7) The width of the waist is 2.5 mm. This may, however, be larger or smaller.

(8) The radius of curvature of the spherical exit pupil centered at point B is 1.5 mm.

(9) The spherical and ellipsoidal surfaces are silvered except for the exit pupil and the waist. The silvered surfaces are black lacquer coated for protection.

(10) The waist consists of a plate with polished surfaces which is used in mounting and possibly also for attaching hydrodynamic focussing cones in flow cytometry and for illumination in laser based instruments.

Figure 4:
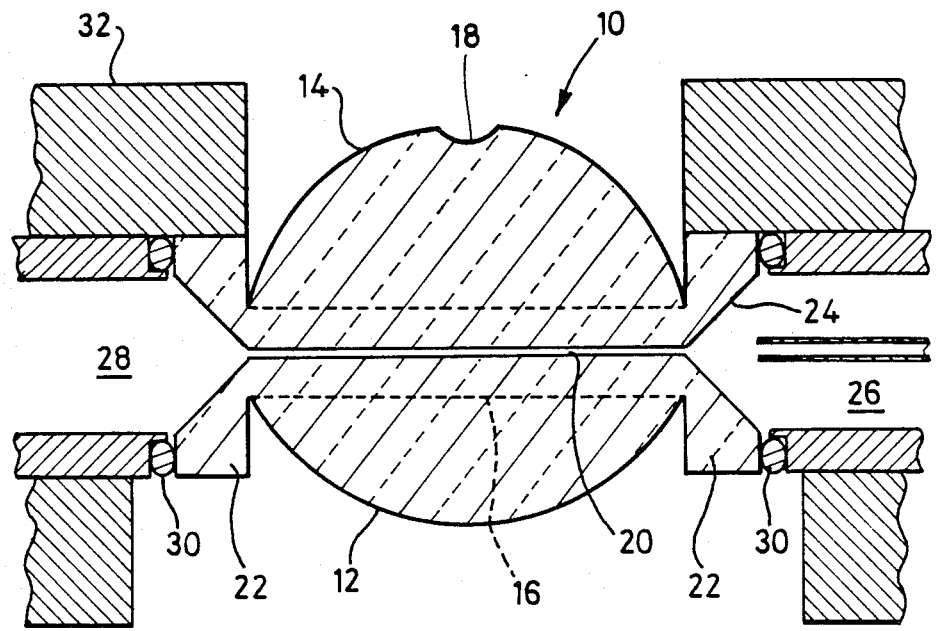
FIG. 4 is a diagrammatic cross section taken along the flow axis in a light collecting device adapted for flow cytometry.

A practical construction of light collecting chamber for use in flow cytometry is shown in FIG. 4. This may have the features and dimensions detailed above and, in addition, a 250 by 250 micrometer square cross-sectioned, internally polished capillary bore 20 passing through the waist and intersecting the first conjugate focus at point A.

The light collecting chamber 10 shown in FIG. 4 may be employed in either a microscope or laser-based instrument. In the former mode, a fluorescence microscope is focussed on the second conjugate focus, i.e. point B in FIG. 3. As the system relies on reflection it is entirely achromatic, as previously mentioned. Thus, all exciting light passing through point B, irrespective of its wavelength, will pass through point A after reflection in the chamber. This gives "all round" illumination of the objects in flow as they pass through point A. Furthermore, all fluorescent light emitted by the objects as they pass through point A will, after reflection, pass through point B. Thus, the excitation and emission light paths are coincident, as is normal in epi-fluorescence microscope applications. In a laser-based system, the beam is focussed directly on to point A through a polished flat on the mounting waist, and again all fluorescent light emitted from point A passes through point B on to which light collection optics are focussed. Light detection may be by means of a camera or a photomultiplier tube.

More particularly, the 2.5 mm thick central plate constituting the waist is used for mounting in microscope applications and is used for inputting the beam in a laser-based instrument. Circular end discs 22, which are integral parts of the chamber 10, contain hydrodynamic focussing cones 24 between which extends the capillary bore 20. The input and output sample tubes 26, 28 are pressure sealed against these discs with 0-rings 30. Reference 32 in FIG. 4 denotes a microscope base.

The above-described device has a light collection efficiency greater than 85 per cent and may be applied in any optical system which requires very high light collection efficiency from a source which is small compared with the size of the device. Specifically in flow cytometry, the device enables a standard fluorescence microscope to double as a flow cytometer, reducing the necessity for expensive laser-based instruments. However, use of the chamber in a laser-based instrument can enable a detection limit equivalent to a few tens of free fluorescein molecules per cell to be achieved, which is well beyond the limits which have hitherto been achievable.

In the described embodiment, the parts 12 and 14 are machined from solid quartz and have silvered reflecting surfaces applied thereto. However, in other applications the light collecting chamber 10 could be formed from a hollow body.

I claim:

1. A light collecting device comprising an internally reflecting chamber for collecting light from a point source within the chamber over a solid angle of substantially 4 pi and directing all the collected light through an exit point at or adjacent the wall of the chamber, said chamber being in the form of an ellipsoidal surface extending over a solid angle of substantially 2 pi and a spherical surface extending over a solid angle of substantially 2 pi, the first conjugate focus of the ellipsoidal surface being coincident with the centre of curvature of the spherical surface and the second conjugate focus of the ellipsoidal surface being located at or adjacent the spherical surface at the centre point of the curved surface area thereof, whereby in use light from a point source located at the said first conjugate focus is directed through the said second conjugate focus, some by virtue of a single reflection at the ellipsoidal surface and the rest by virtue of an initial reflection at the spherical surface followed by a reflection at the ellipsoidal surface.

2. A light collecting device according to claim 1, wherein the ellipsoidal and spherical surfaces are connected through a waist which is used for mounting the device.

3. A light collecting device according to claim 2, wherein the waist is an axially-short cylindrical surface.

4. A light collecting device according to claim 1, wherein a polished light exit pupil is provided in the region of the exit point, cut into the spherical surface with a centre of curvature at the exact exit point, so that all light rays reflected from the ellipsoidal surface are normal to the surface of the pupil, whereby the device is non-refracting and hence completely achromatic.

5. A light collecting device according to claim 1, wherein a capillary bore passes through the said first conjugate focus to accommodate a sample stream for flow cytometry.

6. A light collecting device according to claim 5, wherein illumination to produce fluorescence at the said first conjugate focus is by way of laser light directed through a waist interconnecting the ellipsoidal and spherical surface, or arc-lamp light directed through the exit point to be focussed at the first conjugate focus.

7. A light collecting device according to claim 5, wherein the chamber is formed from laser grade fused silica or quartz, and incorporates integral end discs which are interconnected by the capillary bore which passes through the first conjugate focus, which is coincident with the centre of curvature of the spherical surface.

8. A light collecting device according to claim 7, wherein the chamber is silvered except at the waist and exit pupil, and the silvered surface is black lacquer coated for protection.

* * * * *